United States Patent
Shahar et al.

(10) Patent No.: US 8,231,552 B2
(45) Date of Patent: Jul. 31, 2012

(54) URETHRAL BLOCKAGE DIAGNOSIS

(75) Inventors: Menashe Shahar, Korazim (IL); Ori Sahar, Korazim (IL)

(73) Assignee: P. Square Medical Ltd., Yokneam (IL)

( * ) Notice: Subject to any disclaimer, the term of this patent is extended or adjusted under 35 U.S.C. 154(b) by 766 days.

(21) Appl. No.: 12/158,845

(22) PCT Filed: Dec. 20, 2006

(86) PCT No.: PCT/IL2006/001463
§ 371 (c)(1), (2), (4) Date: Jun. 23, 2008

(87) PCT Pub. No.: WO2007/072484
PCT Pub. Date: Jun. 28, 2007

(65) Prior Publication Data
US 2008/0312538 A1 Dec. 18, 2008

(30) Foreign Application Priority Data
Dec. 22, 2005 (IL) .......................... 172754

(51) Int. Cl.
*A61B 5/00* (2006.01)
*A61B 7/00* (2006.01)
*A61B 5/103* (2006.01)
*A61B 5/117* (2006.01)
*A61M 5/00* (2006.01)

(52) U.S. Cl. ............. 600/586; 600/561; 600/587; 604/9

(58) Field of Classification Search .................. 600/586, 600/587, 561
See application file for complete search history.

(56) References Cited

U.S. PATENT DOCUMENTS

| | | | | |
|---|---|---|---|---|
| 4,802,490 A | * | 2/1989 | Johnston | 600/454 |
| 4,873,990 A | * | 10/1989 | Holmes et al. | 600/561 |
| 5,109,863 A | | 5/1992 | Semmlow et al. | |
| 5,305,751 A | * | 4/1994 | Chopp et al. | 600/409 |
| 5,794,622 A | * | 8/1998 | Chopp et al. | 600/431 |
| 5,807,278 A | * | 9/1998 | McRae | 600/579 |
| 5,823,972 A | * | 10/1998 | McRae | 600/573 |
| 5,853,005 A | | 12/1998 | Scanlon | |
| 5,929,342 A | * | 7/1999 | Thompson | 73/861.04 |

(Continued)

FOREIGN PATENT DOCUMENTS
RU 2 224 464 C2 2/2004
(Continued)

OTHER PUBLICATIONS
Teriö, "Acoustic Method for Assessment of Urethral Obstruction: A Model Study," Medical & Biological Engineering & Computing, Jul. 1, 1991, pp. 450-456, vol. 29, No. 4.

(Continued)

*Primary Examiner* — Sean Dougherty
(74) *Attorney, Agent, or Firm* — Oliff & Berridge, PLC

(57) ABSTRACT

A system and method are provided for the determination of urethral blockage. The system comprises a transducer arrangement for locating in the vicinity of the patient's urine flow, and a control unit in communication with the transducer arrangement. The transducer arrangement has at least one acoustic transducer capable of at least receiving acoustic waves, generated by the patient's urine flow, and producing an output signal indicative thereof. The control unit receives and processes the output signal and determines a change in the output signal indicative of the urethral blockage.

15 Claims, 6 Drawing Sheets

U.S. PATENT DOCUMENTS

| | | | | |
|---|---|---|---|---|
| 5,947,901 | A | * | 9/1999 | Redano .................. 600/439 |
| 6,015,393 | A | * | 1/2000 | Hovland et al. ............... 600/587 |
| 6,063,043 | A | | 5/2000 | Meyer et al. |
| 6,221,021 | B1 | * | 4/2001 | Redano .................. 600/454 |
| 6,251,076 | B1 | * | 6/2001 | Hovland et al. ............... 600/454 |
| 6,325,066 | B1 | * | 12/2001 | Hughes et al. ................ 128/885 |
| 6,354,146 | B1 | * | 3/2002 | Birchak et al. ............... 73/61.79 |
| 6,428,478 | B2 | * | 8/2002 | Redano .................. 600/439 |
| 6,428,479 | B1 | | 8/2002 | Aksnes et al. |
| 6,616,624 | B1 | * | 9/2003 | Kieval ................ 604/8 |
| 6,705,319 | B1 | * | 3/2004 | Wodicka et al. ......... 128/207.14 |
| 6,863,654 | B2 | | 3/2005 | Zappala et al. |
| 7,485,104 | B2 | * | 2/2009 | Kieval ................ 604/9 |
| 7,758,519 | B2 | * | 7/2010 | Brohan et al. ............... 600/584 |
| 7,811,237 | B2 | * | 10/2010 | Brohan et al. ............... 600/584 |
| 2001/0020162 | A1 | * | 9/2001 | Mosel et al. ............... 604/544 |
| 2002/0040185 | A1 | * | 4/2002 | Atalar et al. ............... 600/423 |
| 2002/0049425 | A1 | * | 4/2002 | Mosel et al. ............... 604/544 |
| 2002/0099286 | A1 | | 7/2002 | Sandler et al. |
| 2002/0111586 | A1 | * | 8/2002 | Mosel et al. ............... 604/174 |
| 2003/0199806 | A1 | * | 10/2003 | Kieval ................ 604/8 |
| 2004/0068203 | A1 | * | 4/2004 | Gellman et al. ............ 600/587 |
| 2004/0230120 | A1 | * | 11/2004 | Redano .................. 600/446 |
| 2004/0260163 | A1 | * | 12/2004 | Kron et al. .................... 600/345 |
| 2005/0178395 | A1 | * | 8/2005 | Hunter et al. ................ 128/898 |
| 2005/0215896 | A1 | * | 9/2005 | McMorrow et al. .......... 600/437 |
| 2007/0225616 | A1 | * | 9/2007 | Brown et al. ................ 600/587 |
| 2009/0105631 | A1 | * | 4/2009 | Kieval ................ 604/9 |
| 2011/0125061 | A1 | * | 5/2011 | Shahar et al. ............... 600/586 |

FOREIGN PATENT DOCUMENTS

| | | |
|---|---|---|
| WO | WO 2005/004726 A2 | 1/2005 |
| WO | WO 2005/067392 A2 | 7/2005 |
| WO | WO 2007/072484 A2 | 6/2007 |
| WO | WO 2008/000254 A1 | 1/2008 |

OTHER PUBLICATIONS

Ask et al., "Bio-Acoustic Signals from Stenotic Tube Flow: State of the Art and Perspectives for Future Methodological Development," Medical & Biological Engineering & Computing, Sep. 1, 1995, pp. 669-675, vol. 33, No. 5.

Albright et al., "Diagnosis of Urethral Flow Parameters by Ultrasonic Backscatter," IEEE Transactions on Biomedical Engineering, Jan. 1, 1975, pp. 1-11, vol. BME-22, No. 1.

Idzenga et al., "Perineal Noise Recording as a Non-Invasive Diagnostic Method of Urinary Bladder Outlet Obstruction: A Study in Polyvinyl Alcohol and Silicone Model Urethras," Neurourology and Urodynamics, Jan. 1, 2005, pp. 381-388, vol. 24, No. 4.

Lerner et al,, "Distal Ureteral Calculi: Diagnosis by Transrectal Sonography," American Jouranl of Roentgenology, Dec. 1986, pp. 1189-1191, vol. 147, No. 6.

International Search Report issued in International Patent Application No. PCT/IL2009/000479 mailed on Oct. 28, 2009.

Supplementary European Search Report issued in European Patent Application No. EP 06 82 1648 mailed on Dec. 22, 2009.

Abrams, P.; "Bladder outlet obstruction index, bladder contractility index and bladder voiding efficiency: three simple indices to define bladder voiding function;" *BJU International*; Mar. 1999; pp. 14-15; vol. 84; Bristol, United Kingdom.

"The Pharmacist's Role in the Management of Lower Urinary Tract Symptoms;" *American Pharmacists Association Highlights Newsletter*; Jul. 2004; pp. 1-6; vol. 7—No. 3; United States.

"Prostrate Enlargement: Benign Prostatic Hyperplasia;" NIH Publication No. 04-3012; Feb. 2004; United States.

Jones et al; "Analysis of break frequencies downstream of a constriction in a cylindrical tube;" *J. Biomechanics*; 1987; pp. 319-327; vol. 20—No. 3; Great Britain.

Mastrigt et al., "Towards a noninvasive urodynamic diagnosis of infravesical obstruction", BJU International, Mar. 31, 1999, 84, pp. 195-203.

* cited by examiner

URETHRAL BLOCKAGE DIAGNOSIS

FIELD OF THE INVENTION

This invention is generally in the field of medical devices, and relates to a device and method for quantitative diagnosis of urethral blockage in patients.

BACKGROUND OF THE INVENTION

Prostate enlargement is a widespread phenomenon developed in more than half men over age 50. By age 80, about 80% of men have enlarged prostates. The prostate enlargement is thought to be related to hormonal disorders typical to the age, and is termed Benign Prostatic Hyperplasia or BPH. In a minority of the cases, the prostate enlargement involves prostate cancer.

Whatsoever be the cause, enlarged prostate may lead to bladder control problems. This is because the prostate gland encircles the urethra beneath the bladder neck. An enlarged prostate exerts pressure on the urethra which may deform its shape and reduce its cross sectional area. In acute circumstances, a total blockage of the urethra might occur.

A quantitative diagnosis of the urethral blockage can help in early detection of prostate problems, which in turn allows for anticipating medication or other appropriate treatment. In cases where bladder control problems exist already, a quantitative diagnosis may help in determining severity of the case and in monitoring the effect of the treatment procedures been taken.

From a broader perspective, a quantitative diagnosis of urethral blockage is only one of several common tests taken during the somewhat complicated process of screening and diagnosing for Lower Urinary Tract Symptoms (LUTS). Lower Urinary Tract Symptoms may involve several factors, including disorders in the somatic nervous system, in the bladder/urethral autonomic nervous system, in the detrusor and in the sphincter muscles, and more. Said screening process is therefore a must for distinguishing between the plurality of medical situations that may cause a patient to experience urinary problems.

Facilitating and simplifying the recognition and the quantitative diagnosis of urethral blockage may therefore be essential not only in case a blockage does exist, but also in negating its existence in the opposite case thus leading toward a correct diagnosis.

The methods commonly used for quantitative detection of prostate condition include the following techniques: a digital rectal exam to feel for prostate enlargement; cystoscopy (under local anesthetic) consisting of passing a lens into the urethra and bladder to see if any abnormalities are present; intravenous pyelogram consisting of X-ray irradiation of the urinary tract as a dye is injected into a vein that shows up tumors or blockages; ultrasound test of the prostate. The latter is generally implemented by using one of two methods: Transrectal ultrasonography (TRUS) that uses a rectal probe for assessing the prostate, and can sometimes detect cancer; and Transabdominal ultrasonography that uses a device placed over the abdomen. Comparing TRUS with Transabdominal ultrasonography, TRUS is significantly more accurate for determining prostate volume or the degree of urethral blockage, while Transabdominal ultrasonography can give an accurate measure of postvoid residual urine and is less invasive and expensive than TRUS.

Yet another known technique for quantitative detection of prostate condition is based on the uroflowmetry test. This is aimed at determining whether the bladder is obstructed, by electronically measuring the speed of urine flow. The test, however, cannot determine the cause of obstruction, which can be due not only to BPH, but possibly also to abnormalities in the urethra, weak bladder muscles, or other causes. According to this technique, the patient is instructed not to urinate for several hours before the test and to drink plenty of fluids so he has a full bladder and a strong urge to urinate. To perform this test, a patient urinates into a special toilet equipped with an uroflowmeter. It is important that the patient remains still while urinating to help ensure accuracy, and that he urinates normally and does not exert strain to empty his bladder or attempt to retard his urine flow. Many factors can affect urine flow, such as straining or holding back because of self-consciousness; so experts recommend then that the test be repeated at least twice. The rate of urine flow is calculated as milliliters of urine passed per second (mL/s). At its peak, the flow rate measurement is recorded and referred to as the Q[max]. The higher the Q[max], the better the patients flow rate. Men with a Q[max] of less than 12 mL/s have four times the risk for urinary retention than men with a stronger urinary flow. The Q[max] measurement is sometimes used as the basis for determining the severity of obstruction and for judging the success of treatments. It is not very accurate, however, for a number of reasons: Urine flow varies widely among individuals as well as from test to test. The patient's age must be considered. Flow rate normally decreases as men age, so the Q[max] typically ranges from more than 25 mL/s in young men to less than 10 mL/s in elderly men. The Q[max] level does not necessarily coincide with a patient's perceptions of the severity of his own symptoms.

It is appreciated that the currently used non invasive methods are incapable of individually determining a urethral blockage or performing a quantitative measurement thereof. For example, uroflowmetry may not necessarily teach of a blockage and/or of its severity unless the internal bladder pressure is also known. This is because on the one hand a low flow rate may be an indication of a detrusor problem rather than of a urethral blockage, while on the other hand a normally detected flow rate should not necessarily indicate of a normal urethra since it may result from extra abdominal/bladder pressures compensating against certain flow resistance caused by urethral blockage. Uroflowmetry combined with simultaneous measurement of internal bladder pressure is thus required in order to allow for discrimination between the different factors (i.e. the urethra flow resistance and the abdominal/bladder pressure). Internal bladder pressure measurement involves however invasive procedure—inserting a catheter into the bladder. The inconvenience and infection risks accompanied to the procedure make its use rare and appropriate for special cases only.

U.S. Pat. No. 6,063,043 discloses a passive acoustic method of detecting the presence or absence of vesicoureteral reflux in a patient. According to this technique, sound from the abdomen of the patient from a time just prior to the onset of urination in the patient is amplified, and then the presence or absence of an audio signal characteristic of vesicureteral reflux in the amplified sound is detected. The presence of the signal indicates the presence of vesicoureteral reflux in the patient.

U.S. Pat. No. 6,428,479 discloses a technique of detecting prostate abnormalities such as cancer. This technique utilizes ultrasonic determination of the in-flow kinetics of contrast agent-containing blood in the prostate and/or observation of disease-related asymmetries in the spoke-like vascular pattern of the prostate.

WO 05/067392 discloses a rectal probe adapted for ultrasound and magnetic resonance imaging of the prostate. This probe comprises an ultrasound imaging probe; an MRI probe; and a link joining the ultrasound probe and the MRI probe. The MRI probe comprises a first magnetic field source for creating a static magnetic field in an MRI imaging region outside the rectal probe, a second magnetic field source for creating a time-varying magnetic field which excites nuclei in the MRI imaging region, and a receiver for receiving NMR signals from the excited nuclei and generating MRI imaging data indicative thereof.

WO 05/004726 describes a method of analyzing a Doppler flow image of a region containing a tumor, wherein the region includes a pelvis, adnexa uteri, a uterus, an ovary, a breast, a prostate, a hepatic artery, a liver and the like. According to this technique, the Doppler flow image is represented as a three-dimensional flow representation; and at least one parameter characterizing a velocity spectrum of the three-dimensional flow representation is calculated, so as to determine malignancy likelihood of the tumor; thereby analyzing the Doppler flow image.

U.S. Pat. No. 6,863,654 discloses a method of identifying a patient's urethral anatomic course in real time for the precise placement of a treatment element into the patient's prostate. This technique utilizes a catheter containing an external, inflatable imaging bladder. The catheter is introduced into a urethra of the patient until the image bladder is generally aligned with a treatment site of the prostate. An imaging probe of an imaging device is operatively positioned relative to the treatment site of the prostate and proximate portions of the urethra. The imaging device is activated so as to obtain a real time image of the treatment site of the prostate. The imaging bladder is filled when needed to essentially turn on and define an acoustic interface between the interior of the imaging bladder and the urethral wall. A boundary of the urethra is identified and viewed at the acoustic interface during placement of the treatment element so as to identify proper positioning thereof relative to the urethra.

RU 2224464 discloses a method using ultrasonic Doppler echometric examination of regional prostate blood circulation. Quantitative and qualitative indices are determined. According to this technique, chronic prostatitis is diagnosed by detecting pulsation index greater than 1.1 and venous blood circulation less than 4.5 cm/s relative to those of practically healthy people.

SUMMARY OF THE INVENTION

There is accordingly a need in the art for techniques for non-invasive instant indication of urethral blockage, to thereby assist in shortening and facilitating the process of screening and diagnosing for Lower Urinary Tract Symptoms (LUTS), even before any physical symptoms have actually been experienced by the patient.

The present invention takes advantage of the fact that the urethral blockage causes the urine flow through a channel of a variable cross-sectional dimension, thereby resulting in a turbulence flow of the urine, which is of a differing nature than that of urine flow in normal urethras. The inventors have found that such a turbulence flow of the urine generates acoustic rustles of unique frequencies in partially blocked urethras. Accordingly, the recognition of a rustle typical to a turbulent flow is indicative of the flow obstruction on the urine flow path through the urethra, the frequency and magnitude of which may be indicative of the blockage percentage range and of the distance between the transducer interface and the obstruction's location.

The present invention, according to its one broad aspect, provides a system for the determination of urethral blockage, the system comprising a transducer arrangement having at least one acoustic transducer capable of at least receiving acoustic waves, generated by the patient's urine flow, and producing an output signal indicative of the received acoustic waves; and a control unit in communication with the transducer arrangement for receiving and processing the output signal and determining a change in the electrical output indicative of the urethral blockage.

Preferably, a specifically designed positioning unit is provided for positioning the transducer arrangement in the vicinity of the patient's urine flow such that an acoustic interface of the transducer is in a position for receiving acoustic waves generated by the patient's urine flow.

The control unit may include an amplifier for amplifying the electrical signal. The control unit may include a filtering unit for suppressing background noise, as well as discriminating between signal components of different frequencies. The filtering unit may be configured to separate from the electrical signal the wave components of a predetermined frequency range for the analysis while repealing the wave components of other frequencies. Such filtering unit may be configured either to repeal background noises or to direct wave components of different frequencies for analysis through different algorithms.

According to some embodiments of the present invention, the control unit is preprogrammed with a certain physical model based on the information (reference data) relating to frequency ranges associated with unique acoustic rustles expected to be generated by the urine flow in partially blocked urethras. According to some embodiments the present invention, the model may utilize information relating to the magnitudes of acoustic waves in said frequency ranges. Preferably, the reference data includes different levels (at least two such levels) of acoustic waves' parameter(s) corresponding to different diseased conditions, respectively. The analysis of the received acoustic waves allows for determining the dynamics in the patient's condition.

According to another broad aspect of the invention, there is provided a system for the determination of urethral blockage, the system comprising (i) a transducer arrangement having at least one acoustic transducer capable of at least receiving acoustic waves and producing an output signal indicative of the received acoustic waves; (ii) a positioning unit for positioning the transducer arrangement in the vicinity of the patient's urine flow such that an acoustic interface of the transducer is in a position for receiving acoustic waves generated by the patient's urine flow; and (iii) a control unit in communication with the transducer arrangement for receiving and processing the output signal and determining a change in the electrical output indicative of the urethral blockage.

According to yet another broad aspect of the invention, there is provided a method for use in the determination of urethral blockage, the method comprising: detecting acoustic signals originated by a urine flow during the patient's urination and generating output signals indicative thereof; processing and analyzing said output signals to determine a change in the output signals indicative of a turbulence of the urine flow being thereby indicative of the urethral blockage condition.

According to yet another aspect of the invention, there is provided a transducer positioning unit for use in the above-defined system for the determination of the urethral blockage condition, the transducer positioning unit having adjustable fixation mechanism configured to fixate an interface of at least one transducer to a patient body so as to acquire acoustic waves from patient's urine flow.

Preferably, the transducer arrangement includes a plurality of transducers (at least three transducers, each being at least an acoustic receiver) operating simultaneously during the examination, for acquiring acoustic waves from different locations surrounding the focus of an expected problem, and or at different locations along the penis. The control unit is associated with all the transducers and operates to produce a diagnosis based on the combined acoustic data acquired by the transducers.

The system developed by the inventors provides for a continuous analyzing of the urine flow acoustics during the urination. It should, however, be noted that it is not necessary to use the whole session information for the diagnosis. Any piece of the acoustic information acquired during the urination period may be selected and analyzed independently. Separate analysis of the selected portions of acoustic information of the same session may be compared before a final diagnosis is generated.

Although the system of the present invention requires no timing reference, other timing references may be of help. For example, the system of the present invention may be configured for synchronizing with the operation of an uroflowmetry system, such that the analysis of the electrical signal yielding from the acquired acoustic waves may concurrently involve data indicative of the urine flow rate measured by the uroflowmetry. Such combined analysis of both the acoustic data and the urine flow rate data can be made on a continuous basis along the entire urination cycle under examination.

The transducer positioning unit may be configured so as to enable attachment of the transducer arrangement (its interface) to the patient body, thus receiving acoustic waves originated within the urethra after it has been transmitted through the body tissues. This may for example be a piece of patch, or a ring-like arrangement to be mounted onto a penis.

Alternatively, the transducer positioning unit may be configured so as to enable placing the transducer arrangement (its interface) free in the air for receiving acoustic waves originated within the urethra through a free flow of urine in the air (i.e. by using the urine flow as a medium for transmitting the acoustic wave from its location of origin to a location outside patient's body). This may for example be a ring-like element mountable onto a penis and carrying one or more transducers projecting from the ring so as to be in the urine flow path outside the patient's body.

The transducer positioning unit may have an adjustable fixation mechanism configured to attach the transducer(s) to a patient body so as to acquire acoustic waves generated in response to patient's urine flow. Also, according to some embodiments of the invention, the system for the determination of the urethral blockage condition is configured to determine various other parameters of the urine flow, e.g., the velocity profile. To this end, the transducer arrangement may include acoustic transceivers (which may or may not be the same used for the urethral blockage condition determination) operating in the known Doppler-type measurement mode.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

Figure 1:
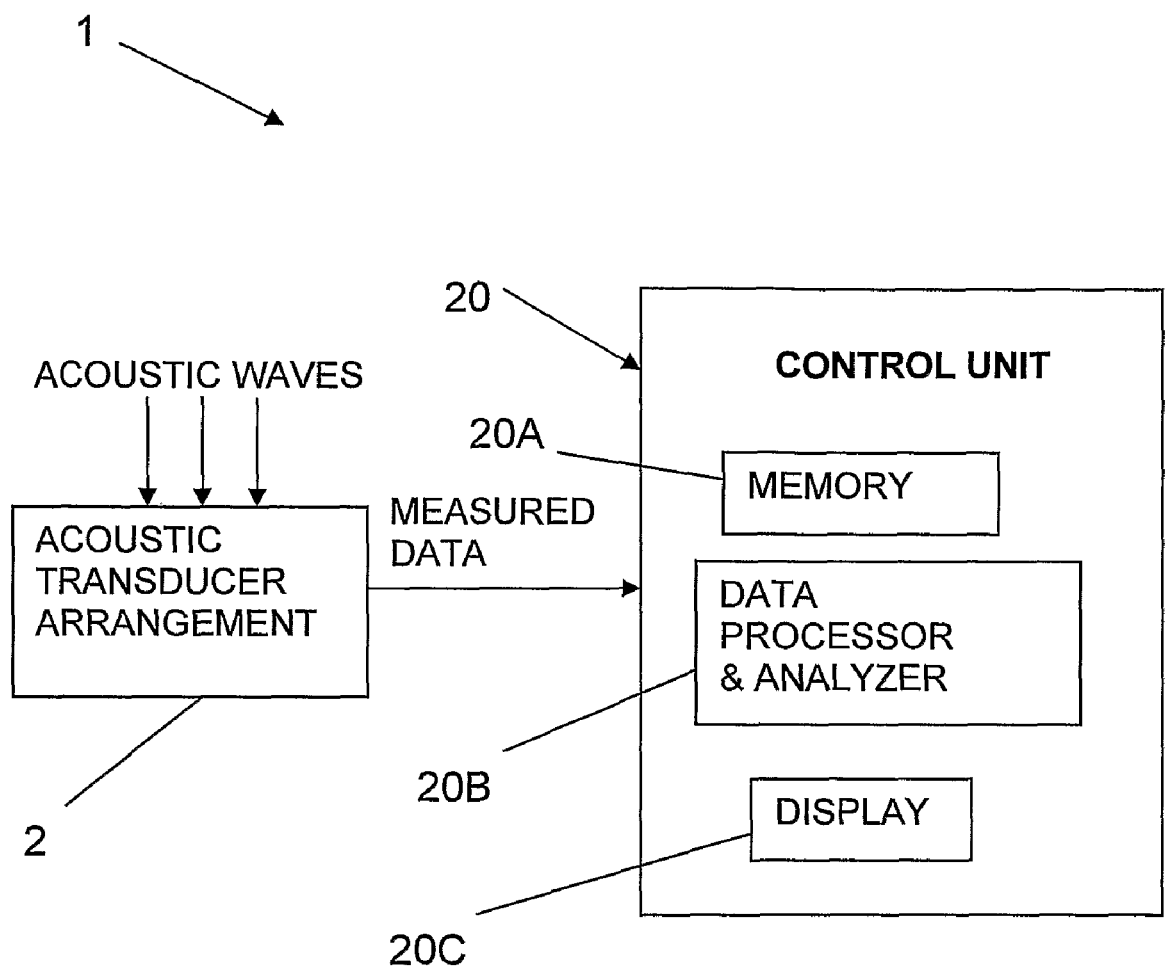
FIG. 1 is a block diagram of the main components of a monitoring system of the present invention for the determination of the urethra blockage condition.

Referring to FIG. 1 there is schematically illustrated an example of a monitoring system 1 of the present invention for monitoring the urethra blockage condition. System 1 includes such main constructional parts as an acoustic transducer arrangement 2 including one or more acoustic transducers capable of at least receiving acoustic waves and generating an electrical output indicative thereof, and a control unit 20 connectable (via wires or wireless signal transmission) to the output of the acoustic transducer arrangement. The latter is carried by a positioning unit (not shown here) to appropriately position the acoustic transducer arrangement 2 with respect to a region of interest.

The acoustic transducer arrangement 2 may include one or more acoustic transceiver. The acoustic transducer arrangement 2 may be a passive unit (which is sufficient for the purposes of the present invention) thus including one or more acoustic receivers (microphones or accelerometers). Such an acoustic receiver may be configured to provide an analog electrical output, or may be equipped with an analog-to-digital converter thus providing digital output indicative of the received acoustic waves.

The system may be configured to determine various urine flow related parameters other than the urethra blockage condition, for example the urine flow velocity profile. To this end, the acoustic transducer arrangement may be configured and operable to implement Doppler-type measurements. The principles of this type of measurements are well known per se and do not form part of the present invention and therefore need not be specifically described, except to note that in this case the transducer arrangement is configured as the so-called "active" unit capable of transmitting acoustic signals towards a region of interest and receiving reflections of these signals from the region of interest.

The control unit 20 is a computer system having inter ala a memory utility 20A (for storing certain reference data as will be described further below), a data processing and analyzing utility 20B (preprogrammed with a predetermined algorithm for analyzing data indicative of the received acoustic waves), and a control panel 20C with a display or any other data presentation utility.

Figure 2:
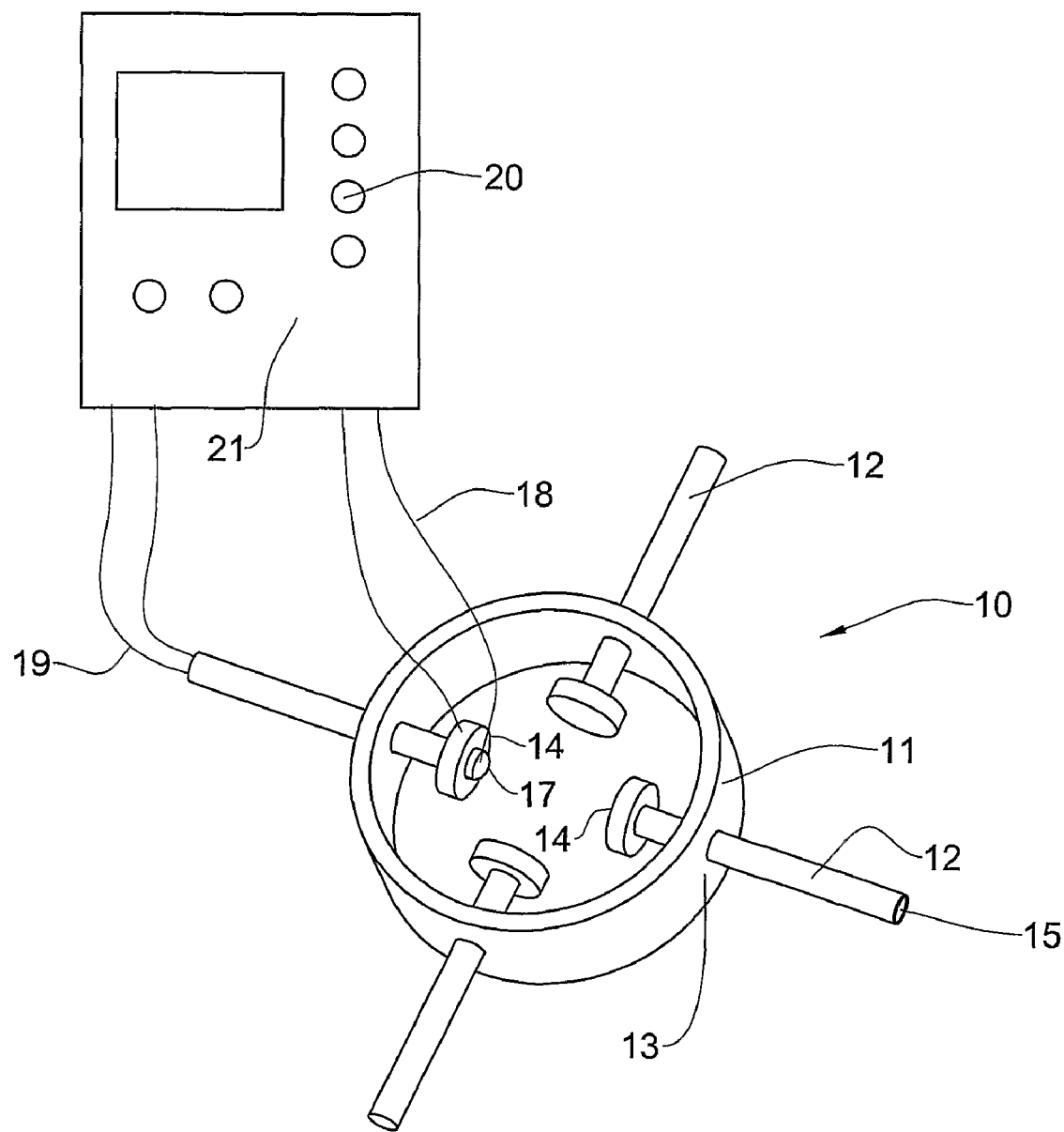
FIG. 2 exemplifies the configuration of an acoustic transducer arrangement suitable to be used in the system of the present invention.

Reference is made to FIG. 2, showing an of the transducer arrangement configuration suitable to be used in the above-described system 1. In the present example, transducer arrangement 2 is formed by four acoustic transducers, generally at 17, arranged in a spaced-apart relationship to form a circular array around the region of interest, i.e., around the urine flow region. It should be understood that the invention is not limited to this specific example, and generally at least one acoustic transducer can be used.

A transducer positioning unit 10 is provided, which in the present example includes a ring-like shaped frame 11 and a plurality of radial shafts 12 (four such shafts in the present example) each passing through a respective aperture 13 formed in the ring frame. Each shaft has a first end 15 outside the frame 11 and a second end 16 inside the frame 11. Each shaft is provided with a plate-like member 14 facing the center of the ring shaped frame. The shafts 12 are preferably moveable through the apertures 13 such that the location of the plates 14 relative to the center of the ring is adjustable by moving the shafts through the apertures 13.

The shafts may be held tight in the apertures due to a friction existing between the inner face of the aperture and the outer surface of the shaft contacting it. According to another embodiment, the shafts may be provided with threading matching that of the apertures, thus the adjustment of the shafts through the apertures is by rotating the shafts like screws. According to yet another embodiment, the shafts are spring biased so as to provide for automatic adaptation of the location of plates 14 to the dimensions of a body part to be sandwiched between each pair of them.

It should be noted that generally, at least one of the plates may carry transducer 17, and the other plates be used for the ring positioning around the body part. Preferably, however, each plate carries the transducer.

Transducer 17 is connectable to control unit 20. Considering wireless connection, transducer 17 and control unit 20 are equipped with appropriate communication utilities based on IR acoustic, or RF signal transmission/reception. In the present specific but not limiting example, transducer 17 is connected through a wiring 18, or through wires 19 passing through the shaft, to control unit 20.

The transducer positioning unit 10 is used by placing it on a patient's penis with the frame 11 circumferences the penis near penis's basis, and by adjusting the shafts to bring the plates 14 into contact with the penis so as the unit being gripped on it. At least one shaft with transducer 17 will preferably be contacting the penis from bellow, closer to the urethra.

After the transducer is held in place accordingly, the patient is requested to urinate, and so data indicative of the received acoustic waves produced by the urine flow is recorded and processed by the control unit 20. The related information indicative of the urine flow condition is displayed.

The urethra blockage condition or various such conditions are identified as a corresponding change of the acoustic waves' parameter(s), such as intensity and/or frequency variation compared to reference data previously created and stored in the memory utility of the control unit. As indicated above, this change is caused by the turbulence nature of urine flow due to the urethra blockage.

Figure 3:
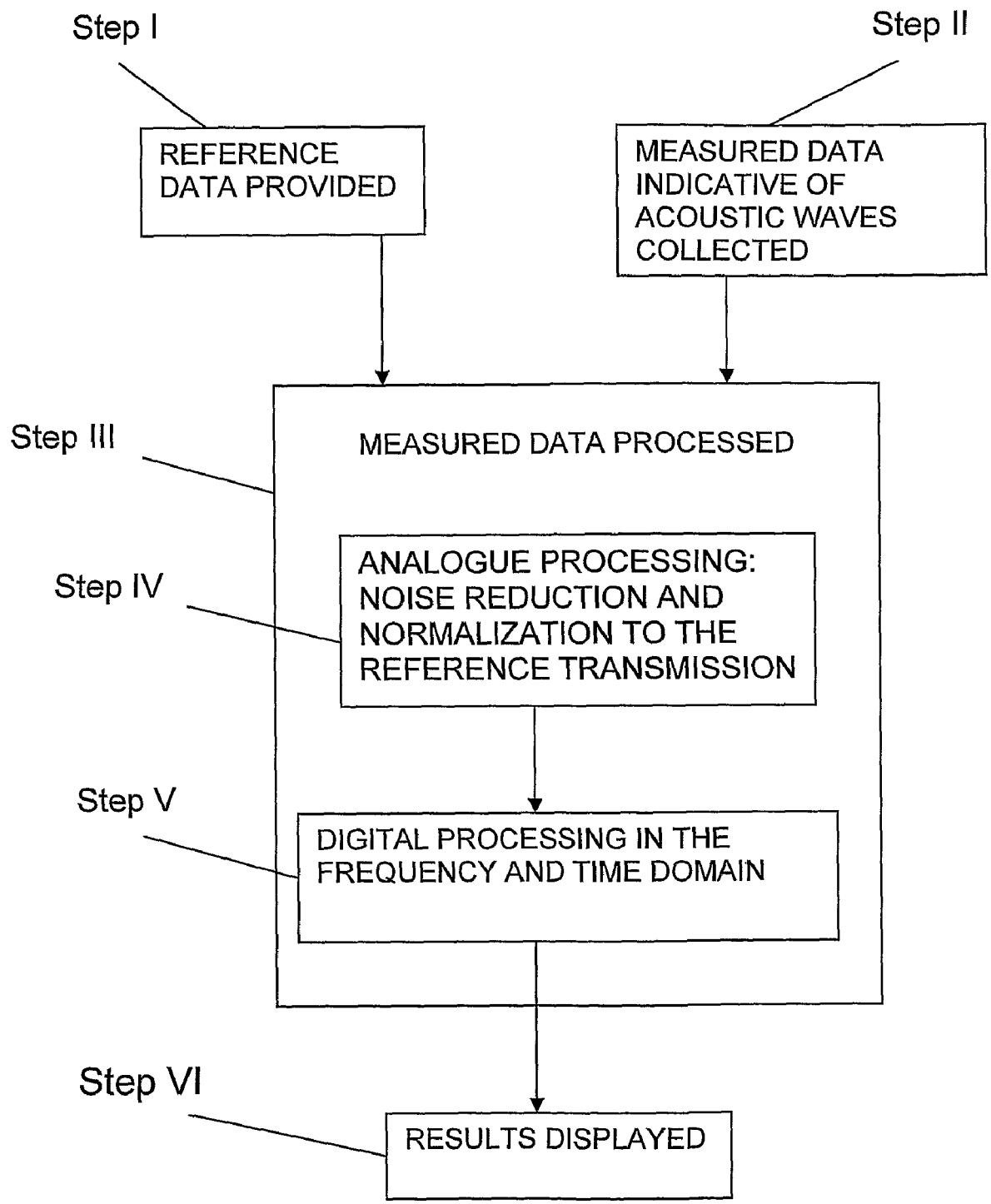
FIG. 3 is a flow diagram of an example of a method of the present invention for use in the determination of the urethra blockage condition.

FIG. 3 exemplifies the method of the present invention for the determination of the urethra blockage condition.

As shown, reference data is provided (step I). The reference data is indicative of the acoustic waves, generated by the urine flow, as a function of frequency and time, for healthy and various different diseased conditions.

Preferably, the reference data include such parameters for different groups of patients, for example of different ages.

Measured data, from a specific patient, is collected (Step II). This measured data is indicative of the acoustic waves received by an array of acoustic transducers from different locations with respect to the urine flow region during the patient's urination. The measured data is in the form of the acoustic waves as function of frequency and time.

The measured data is processed utilizing the reference data (Step III). The processing of the measured data includes analogue processing (Step IV) aimed at noise reduction and normalization to the reference transmission, and digital processing (Step V) of the so-obtained normalized signal in the frequency and time domain.

Generally, all acoustic signals are recorded by first pass through an analog digitizer so to store analog acoustic signal as a digital sequence of amplitude versus time vector. In the present example, such a vector is subject to further signal processing treatment and in particular an FFT (Fast Fourier Transform) filter can be employed in order to extract frequency and phase (compared to a given reference signal) from each signal belonging to each active element (each transducer).

The processed data is compared to the reference data and the comparison results, being indicative of the existence of physiological abnormalities and the degree of pathology, are displayed to the user, who may be a physician or the patient himself (Step VI).

The following are the experimental results of using the technique of the present invention for monitoring the urethral blockage condition. The invention has been exercised on two groups, the first included men of age above 55 who reported of micturition problems (hereinafter "patient group"), and the second included men of age below 30 reported no micturition difficulty (hereinafter "reference group").

The acoustic equipment used for the experiment included a microphone or accelerometer (constituting an acoustic transducer), amplifier and a digital data recorder. It should be noted that the term "accelerometer" is only used here as an example and any other suitable acoustic component may be used.

One possible example of using an accelerometer may be placing it manually at the bottom of the penis as close as possible to the testicles. In this location, the urethra normally reaches its minimal distance from the penis exterior where a transducer (accelerometer) can be placed.

The accelerometer was connected to the input of the amplifier, the output of which was connected to the control unit (its data processor and analyzer utility); it should be understood that amplifier may alternatively be a constructional part of the control unit. The amplifier has been adjusted to 30 dB amplification.

An exemplary result of an examination taken on examinee No. 1 of the patient group in comparison with exemplary result of an examination taken on examinee No. 2 of the reference group will now be explained.

Figure 4:
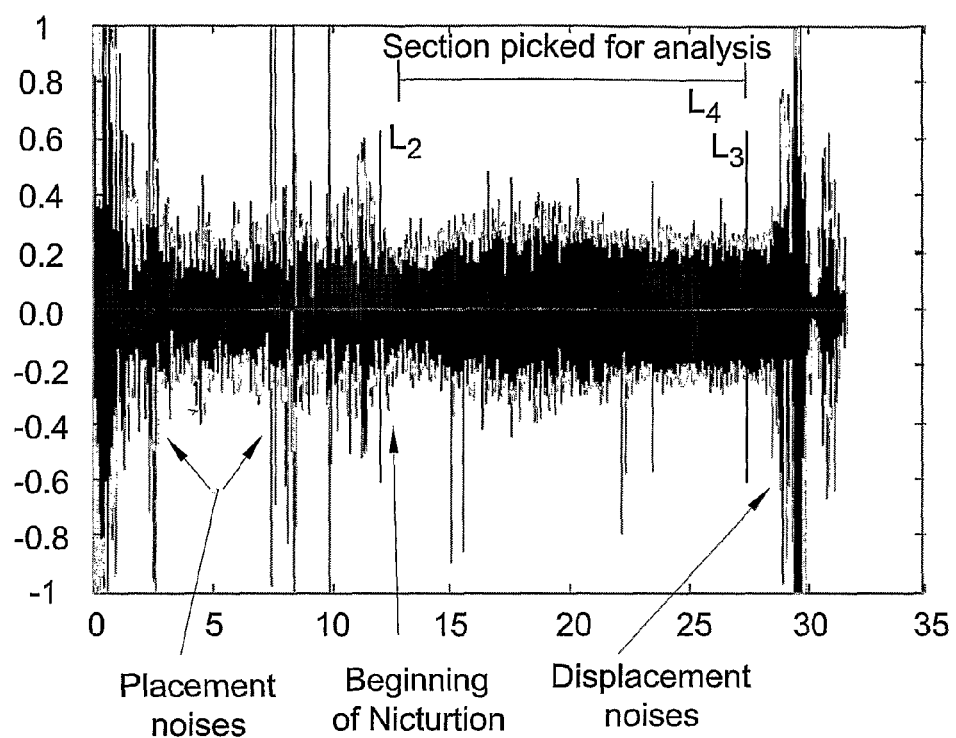
FIGS. 4 to 10 show the experimental results.

FIG. 4 illustrates a graph representing the amplitude versus time of an electrical signal generated by the accelerometer in response to a 32-seconds acoustic wave it has acquired before, during and after the micturition of examinee No. 1.

Micturition starting and ending moments are indicated by vertical lines $L_2$ and $L_3$, respectively. The signals before line $L_2$ and past line $L_3$ are noise signals which include noises of placement and displacement of the accelerometer on the patient body. A section of the micturition interval between lines $L_2$ and $L_3$ marked by horizontal line $L_4$ was picked for analysis. An expanded view of this section is depicted in FIG. 5.

Figure 5:
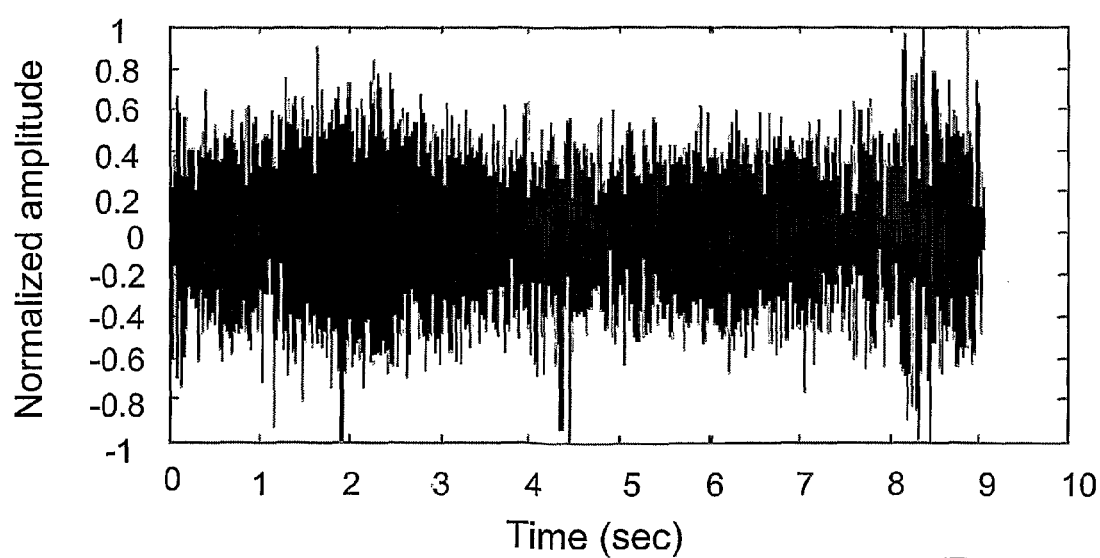

FIG. 5 illustrates an expanded view of a section from the graph illustrated in FIG. 4. The illustrated graph section represents the amplitude versus time of an electrical signal acquired by the accelerometer from the acoustic wave generated during the micturition of examinee No. 1, picked for analysis from the entire graph of FIG. 4.

Figure 6:
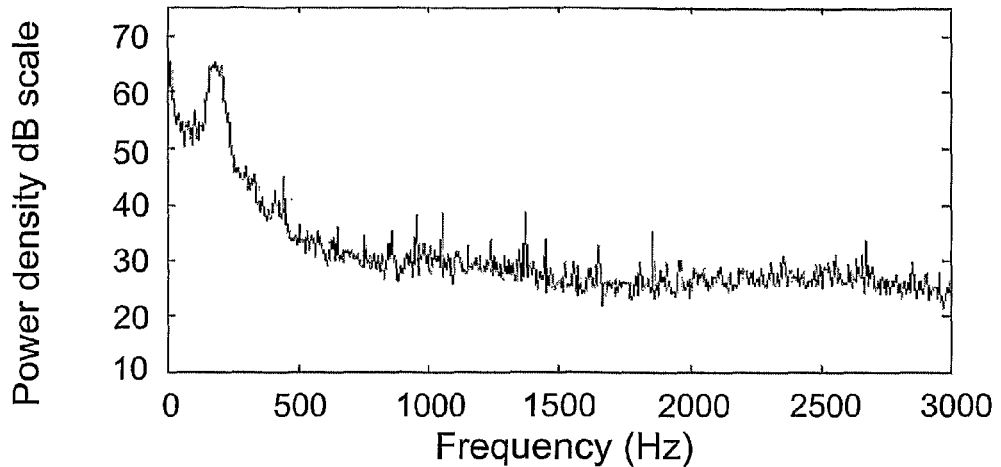
Figure 7:
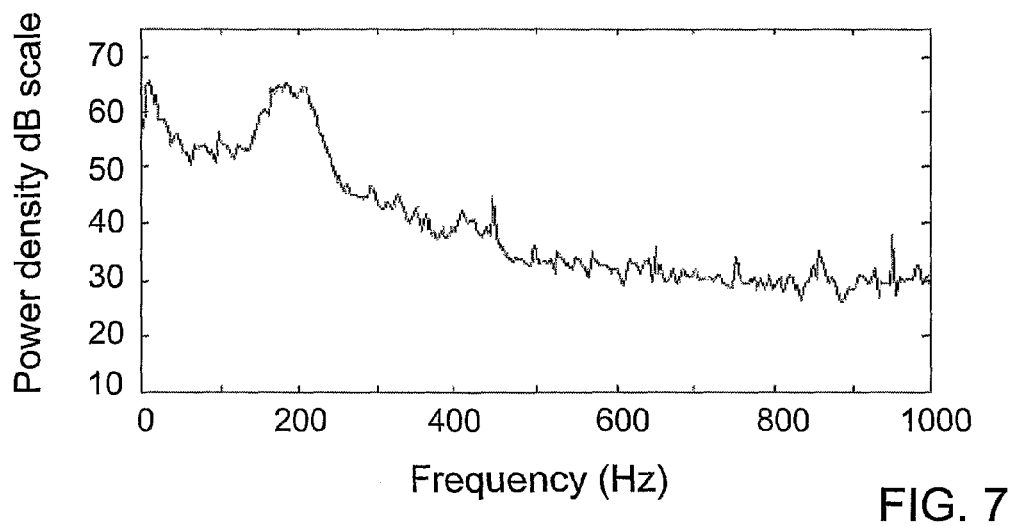

FIG. 6 illustrates a graph of the spectral power density in a dB scale versus wave frequency for the frequency range 0-3 KHz, of the signal section illustrated by FIG. 5. FIG. 7 illustrates an expanded view of the graph illustrated by FIG. 6 for the frequency range 0-1 Khz. As can be noticed, there is a remarkable concentration of acoustic energy in the frequency range around 200 Hz, showing as a hill $H_5$ on the graph line of FIGS. 6 and 7.

Figure 8:
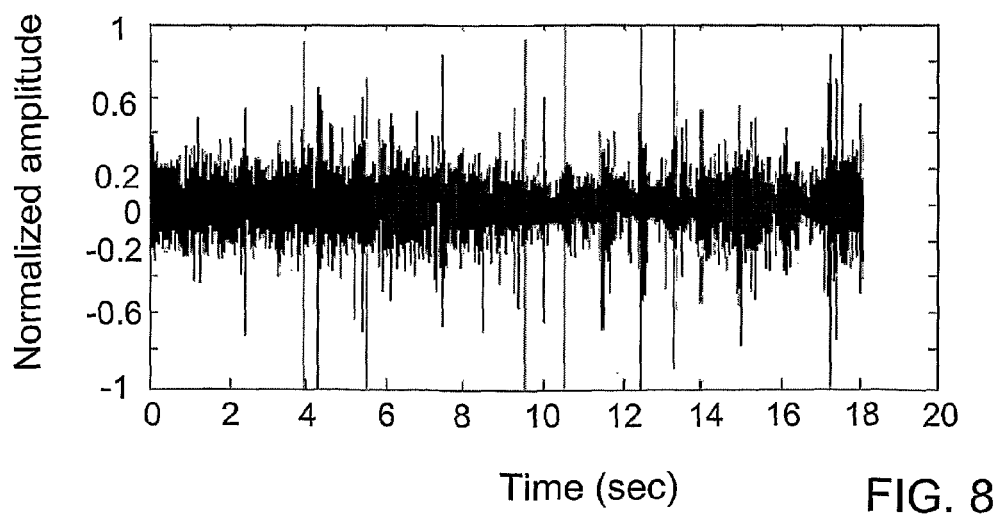
Figure 9:
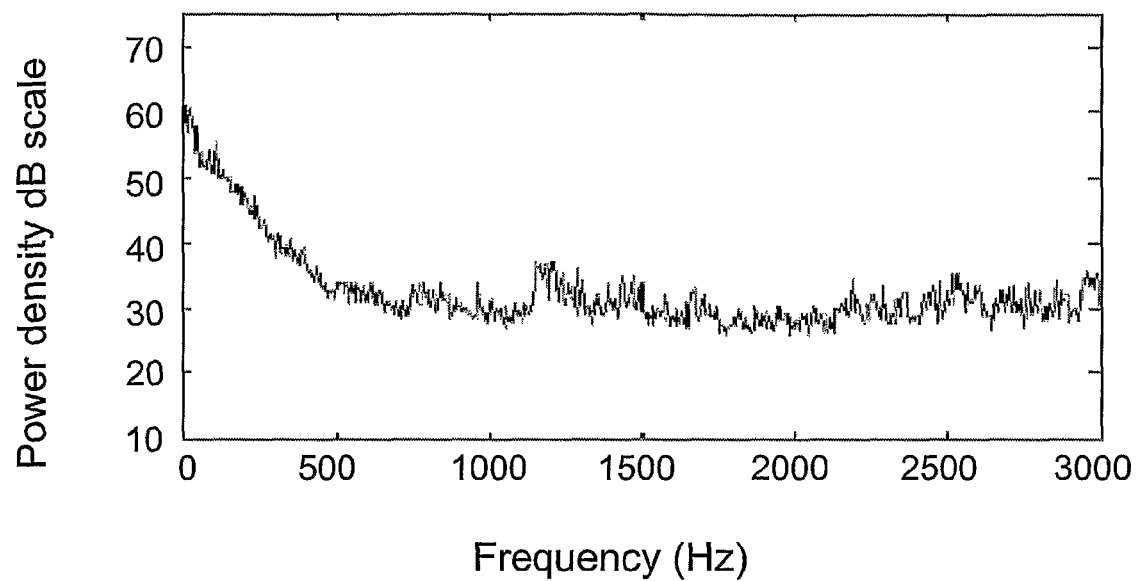
Figure 10:
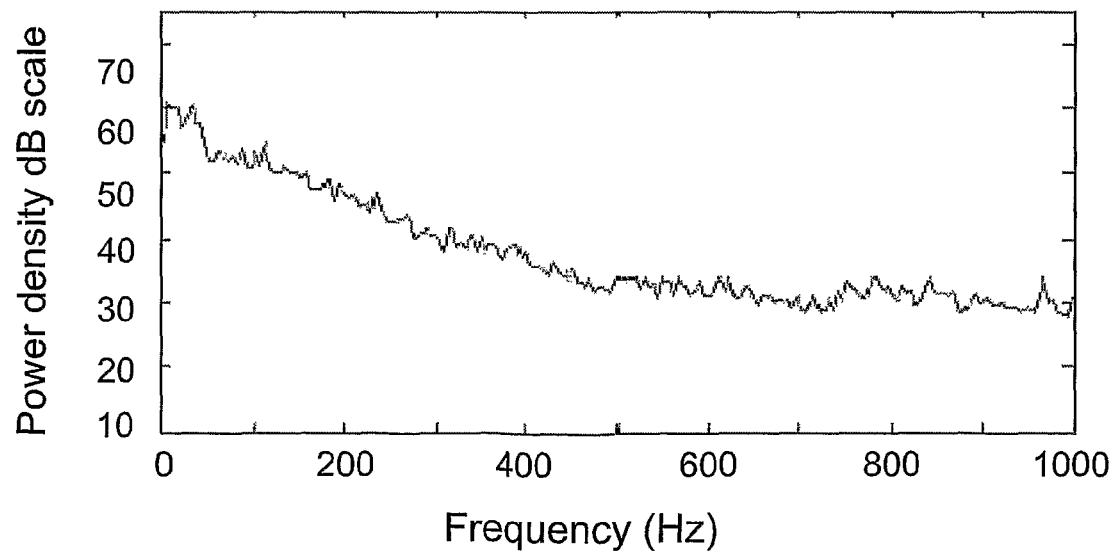

FIGS. 8-10 illustrate mutatis mutandis graphs similar to those illustrated by FIGS. 5-7, taken from the test of examinee No. 2 of the reference group (healthy examinee). As can be observed, no remarkable hill is recognizable in the graph taken from the test of the examinee of the reference group. A comparison between the two graphs leads to the conclusion that the remarkable energy concentration in the 200 Hz frequency range in the graph of examinee No. 1 corresponds to a urethral blockage pathology possibly resulting from BPH of examinee No. 1.

This particular example only partially demonstrates the invention. It should be understood that the invention could utilize various other aspects of the signal analysis, such as phase analysis; comparison between different signals taken simultaneously from different components at different location, etc.

Those skilled in the art will readily appreciate that various modifications and changes can be applied to the embodiments of the invention as herein described without departing from its scope defined in and by appended claims.

The invention claimed is:

1. A system for determination of urethral blockage, the system comprising:
    a transducer arrangement capable of at least receiving acoustic waves, said transducer arrangement being configured such that, when located in a vicinity of a patient's urine flow, the transducer arrangement receives acoustic waves generated by the patient's urine flow at different locations of the urine flow, and produces combined acoustic data indicative of said acoustic waves generated by the patient's urine flow; and
    a control unit in communication with the transducer arrangement, said control unit being configured and operable for receiving and processing said combined acoustic data generated by the transducer arrangement, generating measured data in a form of the acoustic waves as a function of frequency and time, processing said measured data using predetermined reference data and determining a change in the combined acoustic data indicative of a turbulence of the urine flow caused by the urethral blockage.

2. The system of claim 1, further comprising:
    a positioning unit for positioning the transducer arrangement in the vicinity of the patient's urine flow such that an acoustic interface of an acoustic transducer of said transducer arrangement is in a position for receiving acoustic waves generated by the patient's urine flow.

3. The system of claim 1, wherein the control unit is preprogrammed for determining an acoustic rustle of a frequency from 20-1000 Hz.

4. The system of claim 1, wherein the control unit is preprogrammed for determining an acoustic rustle of a frequency of about 200 Hz.

5. The system of claim 1, wherein the transducer arrangement comprises a plurality of acoustic transducers each being capable of at least receiving acoustic waves, said plurality of acoustic transducers being arranged in a spaced-apart relationship for collecting the acoustic waves at the different locations with respect to the urine flow.

6. The system of claim 2, wherein the positioning unit is configured as a ring-like frame for mounting onto a patient's penis.

7. The system of claim 6, wherein said ring-like frame carries a circular array of the acoustic transducers.

8. The system of claim 6, wherein said ring-like frame has an array of spaced-apart apertures and a corresponding array of shafts, the shafts being mounted in the apertures, respectively, and each of the shafts being formed with a plate-like member at the shaft's distal end inside the ring, at least one of the plates carrying at least one of the acoustic transducers.

9. The system of claim 6, wherein said ring-like frame has an array of spaced-apart apertures and a corresponding array of shafts, the shafts being mounted in the apertures, respectively, and each of the shafts being formed with a plate-like member at the shaft's distal end inside the ring carrying one of the acoustic transducers.

10. The system of claim 1, wherein the transducer arrangement comprises one or more acoustic transceivers, the system being configured and operable for carrying out Doppler-type measurements of one or more parameters of the urine flow.

11. The system of claim 5, wherein at least two of said plurality of acoustic transducers are configured as acoustic transceivers, the system being configured and operable for carrying out Doppler-type measurements of one or more parameters of the urine flow.

12. A system for determination of urethral blockage, the system comprising:
    a transducer arrangement capable of at least receiving acoustic waves and producing an output signal indicative thereof;
    a positioning unit for positioning the transducer arrangement in a vicinity of a patient's urine flow such that an acoustic interface of an acoustic transducer of said transducer arrangement is in a position for receiving acoustic waves generated by the patient's urine flow, the transducer arrangement being configured for receiving acoustic waves generated at different locations of the urine flow and generating combined acoustic data indicative of the received acoustic waves; and
    a control unit in communication with the transducer arrangement, the control unit being configured and operable for receiving and processing the combined acoustic data, generating corresponding measured data in a form of a function of frequency and time, processing said measured data utilizing predetermined reference data and determining a change in the combined acoustic data indicative of a turbulence of the urine flow caused by the urethral blockage.

13. A method for use in determination of urethral blockage, the method comprising:
    detecting acoustic signals originated by a urine flow during a patient's urination at different locations along the urine flow, and generating combined acoustic data indicative of said acoustic waves generated by the patient's urine flow;
    processing and analyzing said combined acoustic data;
    generating corresponding data as a function of frequency and time; and
    processing said corresponding data utilizing predetermined reference data to determine a change in the combined acoustic data indicative of a turbulence of the urine flow being thereby indicative of a urethral blockage condition.

14. A method for comparing between acoustic wave generated by urination flow through urethra and between a predetermined criteria, the method comprising
    capturing acoustic waves from different locations along a urine flow,
    converting the acoustic waves to electrical signals,
    delivering the electrical signals to a data processing unit,
    exercising a predetermined algorithm on the electrical signals to generate corresponding digital data indicative of combined acoustic data in a form of a function of frequency and time, and to extract data comparable with the predetermined criteria from the digital data, and comparing between the extracted data and the predetermined criteria to determine a presence of a urethral blockage.

15. The system of claim 5, wherein said plurality of acoustic transducers located at different locations with respect to the patient's urine flow are operable for simultaneously acquiring acoustic waves from said different locations, and said combined acoustic data corresponds to acoustic waves simultaneously measured at the different locations of the urine flow.

* * * * *